United States Patent [19]

Vlasblom

[11] Patent Number: 5,462,729
[45] Date of Patent: Oct. 31, 1995

[54] HOOF AND NAIL CONDITIONER

[75] Inventor: Jack Vlasblom, Dunedin, Fla.

[73] Assignee: Citra Science Ltd., Largo, Fla.

[21] Appl. No.: 287,827

[22] Filed: Aug. 9, 1994

[51] Int. Cl.[6] ........................................................ A61K 7/04
[52] U.S. Cl. ................................................ 424/61; 424/401
[58] Field of Search ........................................ 424/61, 401

[56] References Cited

U.S. PATENT DOCUMENTS

| | | | |
|---|---|---|---|
| 4,070,451 | 1/1978 | Price | 424/61 |
| 4,818,520 | 4/1989 | Fleischner | 424/61 |

FOREIGN PATENT DOCUMENTS 1111934  5/1968  United Kingdom.

OTHER PUBLICATIONS

CA 91: 216678d (1979).
CA 117: 118230n (1992).

*Primary Examiner*—Thurman K. Page
*Assistant Examiner*—Jyothsna Venkat
*Attorney, Agent, or Firm*—Donald R. Fraser

[57] ABSTRACT

A hoof and nail conditioner consists of (2, 5-dioxide-4-imidazolidinyl) urea; pantothenal; ethoxylated lanolin; hydrolyzed keratin protein; sorbitan monolaurate; an antimicrobial preservative; and water.

21 Claims, No Drawings

HOOF AND NAIL CONDITIONER

FIELD OF THE INVENTION

This invention relates generally to a formulation for a hoof and nail conditioner. More particularly, the invention is directed to a formulation which, when applied to the hoofs of animals or nails of humans, conditions and enhances said hoofs and nails.

BACKGROUND OF THE INVENTION

Formulations useful for conditioning the hoofs of animals and nails of humans are known in the art. It would be desirable to prepare a formulation which, when sprayed on or otherwise applied to the hoofs of animals or nails of humans, would effectively restore same to a healthy condition, and reduce cracking and deterioration in said hoofs and nails.

SUMMARY OF THE INVENTION

Accordant with the present invention an improved hoof and nail conditioner has surprisingly been discovered. It consists of: (2, 5-dioxo-4-imidazolidinyl) urea; pantothenol; ethoxylated lanolin; hydrolyzed keratin protein; sorbitan monolaurate; an antimicrobial preservative; and water.

The hoof and nail conditioner of the present invention is particularly useful for conditioning and enhancing the hoofs of horses.

Further objects and advantages of this invention will be apparent from the following description and appended claims.

DETAILED DESCRIPTION OF THE PREFERRED EMBODIMENTS

The formulation of the present invention consists of a precise combination of (2, 5-dioxide-4-imidazolidinyl) urea; pantothenol; ethoxylated lanolin; hydrolyzed keratin protein; sorbitan monolaurate; an antimicrobial preservative; and water.

The (2, 5-dioxo-4-imidazolidinyl) urea is a healing agent employed in the inventive formulation. It may be present at a concentration from about 0.02 to about 1.6 weight percent. Preferably, the concentration is about 0.05 weight percent. A preferred (2, 5-dioxo-4-imidazolidinyl) urea may be obtained from International Sourcing Inc. of Upper Saddle River, N.J. under the product designation "ALLANTOIN".

The conditioner formulation includes pantothenol, a well-known alcohol having vitamin activity. Pantothenol may be present in the inventive formulation at a concentration from about 0.05 to about 4 weight percent. Preferably, the concentration is about 1 weight percent.

The inventive conditioner contains ethoxylated lanolin, a well-known hydrous wax. The ethoxylated lanolin may be present at a concentration from about 0.05 to about 9 weight percent. Preferably, the concentration is about 3 weight percent. A preferred ethoxylated lanolin may be obtained from Amerchol Corporation of Edison, N.J. under the product designation "SOLULAN L-575".

Hydrolyzed keratin protein is included in the inventive formulation. The hydrolyzed keratin protein may be present at a concentration from about 1 to about 9 weight percent. Preferably, the concentration is about 5 weight percent. A preferred hydrolyzed keratin protein may be obtained from Brooks Industries Inc. of South Plainfield, N.J. under the product designation "HYDROKERATIN AL-SD".

Sorbitan monolaurate is included in the conditioner as a stabilizer. The sorbitan monolaurate may be present at a concentration from about 0.03 to about 3 weight percent. Preferably, the concentration is about 1 weight percent.

The inventive conditioner includes an antimicrobial preservative, to prevent microbial degradation. Examples of various antimicrobial agents, as well as their characteristics and method of preparation, are set forth in Kirk-Othmer, "Concise Encyclopedia of Chemical Technology," John Wiley & Sons, New York (1985) at pp 104–106. Preferred antimicrobial preservatives include a blend of isothiazolinones available from Rohm and Haas Company of Philadelphia, Pa. under the product designation "KATHON CG/ICP", and a blend of diazolidinyl urea, methylparaben, and propylparaben in propylene glycol available from Sutter Laboratories of Chateau, N.J. under the product designation "GERMABEN II-E", as well as mixtures thereof. The antimicrobial preservative may be present at a concentration from about 0.01 to about 3.5 weight percent. Preferably, the concentration is about 0.05 weight percent.

Water constitutes the balance of the conditioner, according to the present invention.

The ingredients may be combined and mixed together in conventional high shear mixing equipment, to prepare a conditioner which may then be sprayed or otherwise applied to the hoofs of animals or the nails of humans, to condition same.

In accordance with the provisions of the patent statutes, the present invention has been described in what is considered to represent its preferred embodiment. However, it should be understood that the invention can be practiced otherwise than as specifically illustrated and described without departing from its spirit or scope.

EXAMPLE

The following ingredients are mixed together in the approximate weight percentages indicated, to formulate a hoof and nail conditioner according to the present invention.

TABLE 1

| CONDITIONER | |
|---|---|
| Ingredient | Weight Percent |
| (2, 5-dioxo-4-imidazolidinyl) urea (1) | 0.05 |
| pantothenol | 1 |
| ethoxylated lanolin | 3 |
| hydrolyzed keratin protein (2) | 5 |
| sorbitan monolaurate | 1 |
| preservative (3) | 0.05 |
| water | 89.9 |

(1) ALLANTOIN, from International Sourcing Inc.
(2) HYDROKERATIN AL-SD, from Brooks Industries Inc.
(3) KATHON CG/ICP, from Rohm & Haas.

This Example may be repeated with similar success by substituting the generically or specifically described ingredients and/or concentration recited herein for those used in the preceding Example.

From the foregoing description, one ordinarily skilled in the art can easily ascertain the essential characteristics of this invention and, without departing from its spirit or scope, can make various changes and modifications in the invention to adapt it to various usages and conditions.

What is claimed is:

1. A hoof and nail conditioner, consisting of:

(2,5-dioxo-4-imidazolidinyl) urea;

pantothenol;

ethoxylated lanolin;

hydrolyzed keratin protein;

sorbitan monolaurate;

an antimicrobial preservative; and water.

2. The hoof and nail conditioner according to claim 1, wherein the concentration of (2,5-dioxo-4-imidazolidinyl) urea ranges from about 0.02 to about 1.6 weight percent.

3. The hoof and nail conditioner according to claim 2, wherein the (2,5-dioxo-4-imidazolidinyl) urea concentration is about 0.05 weight percent.

4. The hoof and nail conditioner according to claim 1, wherein the concentration of pantothenol ranges from about 0.05 to about 4 weight percent.

5. The hoof and nail conditioner according to claim 4, wherein the pantothenol concentration is about 1 weight percent.

6. The hoof and nail conditioner according to claim 1, wherein the concentration of ethoxylated lanolin ranges from about 0.05 to about 9 weight percent.

7. The hoof and nail conditioner according to claim 6, wherein the concentration of ethoxylated lanolin is about 3 weight percent.

8. The hoof and nail conditioner according to claim 1, wherein the concentration of hydrolyzed keratin protein ranges from about 1 to about 9 weight percent.

9. The hoof and nail conditioner according to claim 8, wherein the hydrolyzed keratin protein concentration is about 5 weight percent.

10. The hoof and nail conditioner according to claim 1, wherein the concentration of sorbitan monolaurate ranges from about 0.03 to about 3 weight percent.

11. The hoof and nail conditioner according to claim 10, wherein the monolaurate concentration is about 1 weight percent.

12. The hoof and nail conditioner according to claim 1, wherein the concentration of antimicrobial preservative ranges from about 0.01 to about 3,5 weight percent.

13. The hoof and nail conditioner according to claim 12, wherein the antimicrobial preservative concentration is about 0.05 weight percent.

14. A hoof and nail conditioner, consisting of:

from about 0.02 to about 1.6 weight percent (2,5-dioxo-4-imidazolidinyl) urea;

from about 0.05 to about 4 weight percent pantothenol;

from about 0.05 to about 9 weight percent ethoxylated lanolin;

from about 1 to about 9 weight percent hydrolyzed keratin protein;

from about 0.03 to about 3 weight percent sorbitan monolaurate;

from about 0.01 to about 3.5 weight percent of an antimicrobial preservative; and the balance, water.

15. The hoof and nail conditioner according to claim 14, wherein the (2, 5-dioxo-4-imidazolidinyl) urea concentration is about 0.05 weight percent.

16. The hoof and nail conditioner according to claim 14, wherein the pantothenol concentration is about 1 weight percent.

17. The hoof and nail conditioner according to claim 14, wherein the ethoxylated lanolin concentration is about 3 weight percent.

18. The hoof and nail conditioner according to claim 14, wherein the hydrolyzed keratin protein concentration is about 5 weight percent.

19. The hoof and nail conditioner according to claim 14, wherein the sorbitan monolaurate concentration is about 1 weight percent.

20. The hoof and nail conditioner according to claim 14, wherein the antimicrobial preservative concentration is about 0.05 weight percent.

21. A hoof and nail conditioner, consisting of:

about 0.05 weight percent (2,5-dioxo-4-imidazolidinyl) urea;

about 1 weight percent pantothenol;

about 3 weight percent ethoxylated lanolin;

about 5 weight percent hydrolyzed keratin protein;

about 1 weight percent sorbitan monolaurate;

about 0.05 weight percent of an antimicrobial preservative; and the balance, water.

\* \* \* \* \*